United States Patent [19]

Cotter

[11] Patent Number: 5,115,139
[45] Date of Patent: May 19, 1992

[54] BRACKET DEVICE AND METHOD OF ADJUSTABLE FIELD SHAPING FOR EXTERNAL BEAM RADIATION THERAPY TREATMENT

[76] Inventor: Gregory W. Cotter, 5709 Marquis Ct., Mobile, Ala. 36609

[21] Appl. No.: 604,664

[22] Filed: Oct. 29, 1990

[51] Int. Cl.⁵ ............................................. H01J 37/09
[52] U.S. Cl. ............................. 250/505.1; 250/515.1; 378/65
[58] Field of Search ............... 250/515.1, 505.1, 492.1; 378/65

[56] References Cited

U.S. PATENT DOCUMENTS

| | | |
|---|---|---|
| 3,944,838 | 3/1976 | Gäde ................................ 250/515.1 |
| 4,158,779 | 6/1979 | Rommel et al. ................. 250/515.1 |
| 4,214,167 | 7/1980 | Gäde ................................ 250/515.1 |
| 4,266,139 | 5/1981 | Sportelli et al. ................. 250/515.1 |
| 4,472,637 | 9/1984 | Sportelli et al. ................. 250/515.1 |
| 4,642,572 | 2/1987 | Menor ............................. 250/505.1 |
| 4,663,531 | 5/1987 | Ruike ............................. 250/505.1 |

Primary Examiner—Bruce C. Anderson
Attorney, Agent, or Firm—Gregory M. Friedlander

[57] ABSTRACT

A new, device for adjustable field shaping for external-beam radiation therapy is described. The system employs connection flanges defining slots which are mounted to shielding blocks attached to designed blocking trays having slots in order to provide a maximum amount of rotational and lateral movement of the shielding blocks.

10 Claims, 4 Drawing Sheets

BRACKET DEVICE AND METHOD OF ADJUSTABLE FIELD SHAPING FOR EXTERNAL BEAM RADIATION THERAPY TREATMENT

BACKGROUND OF THE INVENTION

PRIOR ART

The invention applies to electromagnetic field shaping devices.

More particularly the device applies to medically related electromagnetic field shaping devices for shaping internal fields and periphery or perimeter fields.

Numerous methods for shaping external beam radiation therapy fields have been developed. These include custom milling or casting of lead blocks and the use of lead shot either poured into styrofoam forms or incorporated into wax. Fordham, E. W.; Gibbs, G. G.; Henderickson, F. R., *Shield Construction of extended field therapy of Hodgkins's Disease*, Radiology 92: 1374–1376 (1969). Page, V.; Gardner, A.; Karzmark, C. J.; *Physical and Dosemtric aspects of the radiotherapy of malignant lymphomas*, Radiology 96: 609–618, (1970); Edland, R. W., Hansen, H.; *Irregular field Shaping for Co-60 teletherapy Radiology* 92: 634–635 (1969); Custom field shaping using cast Lipowitz's metal, however, has probably become the most common method of producing irregular shaped fields for external beam radiation therapy treatment. Radiology 108: 407–411, (1973); Powers, W. E., Kinzle, J. J., Demidecki, A. J., Bradfields, J. S., Feldman, A. *A new system of field shaping for external-beam radiation therapy Radiology* 48: 924–926, (1975); Marshall, T. J., Mott, G. T., Grieveson, J. H. *A technique for using low melting point alloy for individual patient shielding in radiology* Applied Radiology 6: 115, (1977); Luk, K. H., Castro, J. R., Meyler, T. S., Potter, L., Purser, P. R. *Individual low-melting alloy shielding blocks for external-beam radiation therapy* American Institute of Physics, 456–476, (1983); Purdy, J. A. Secodanring Field Shaping In: Wright, A. E. and Boyer, A. L. eds, *Advancing in Radiation Therapy Treatment Planning*, New York, N.Y. Specialized applications for field shaping or tissue shielding have included construction of individualized midline blocks for external beam treatment of pelvic malignancies and gonadal shields in the treatment of lymphoid malignancies. Radiology 107: 611–614, (1973); Walz, B. J., Perez, C. A., Feldman, A., Demidecki, A. J., Powers, W. E., *Individualized compensating filters and dose optimization in pelvic irradiation* Radiology 117: 226(1975) Purdy, J. A., Stiteler, R. D., Glasgow, G. P., Mill, W. B., Gonadal Shield. Other specialized blocking applications have included construction of individualized irregular field blocks for electron beam and superficial X-ray treatment. Int. J. Radia. Onc. Biol. and Phys. 2: 791–795, (1977); Goede, M. R., Gooden, D. S., Ellis, R. G., Brickner, T. J., Jr., *A versatile electron collimation system to be used with electron cones supplied with Varian's Clinac* 18. Radiology 132: 490, (1979); Purdy, J. A., Abrath, F. G., Perez, C. A., *Field shaping for electron-beam radiation therapy*. Br. J. Radiol. 54: 805–807 (1981); Baily, B., Coe, M. A., Hearnden, T. M., *A new technique for radiation shielding in superficial x-ray therapy*.

Irregular field shaping in external beam radiation therapy treatment has allowed treatment of areas of interest and sparing of uninvolved normal tissues. Casting of Lipowitz's metal and similar alloys to produce customized irregular fields is well accepted in many departments. Hand blocks, however, continue to be used for shielding in some cases. The method of adjustable field blocking described in this report is clinically useful and can fill the gap between a full custom block and simple hand blocks in appropriate cases. Advantages of this system include rapid field set up easy field adjustment and improved day to day reproducibility of field set up compared to simple hand blocks. The blocking system is cost effective and has been shown to produce high quality treatment in clinical use.

Custom shaped shielding blocks of Lipowitz's metal and similar allows improve the uniformity of daily treatment fields and are easy to use once they are constructed. Constructing shielding blocks from Lipowitz's metal, however, requires significant time and materials. Some clinical treatment situations frequently do not require a full customized field block. Palliative cases where fields are commonly shaped by simple hand blocks are an example. Other examples include some whole pelvic fields, some simple head and neck fields and some supraciavicular/auxiliary fields where shoulder blocking is required. Daily field shaping using simple hand blocks connected to standard blocking trays, such as in the case of lateral and angled fields, may allow only limited positioning further complicating field setup.

Support plates with slots having shielding members disposed in the slot by way of an adjustable and removable securing means and removable securing means where the slots are transversally mounted other slots. These shielding means are often made in the shape of the organ to be protected. U.S. Pat. Nos. 4,472,637 and 4,266,139 by Sportell, et al exhibit this technique. The most important drawback which these techniques and patents attempt to address is maximizing the flexibility of the system to provide different field shapes for internal blocking as opposed to perimeter fields.

The present patent not only allows for internal blocking but also allows for perimeter field blocking.

The prior art encompasses the use of slotted trays and blocks for mounting thereon. Shielding block molds are fashioned at the appropriate target to tray distance for the external beam treatment unit from high density polyethylene foam using a hot wire cutting device. Lipowitz's metal or similar alloys have been used to cast the shielding blocks and, milled or cast lead blocks may also be used.

It is desirable to minimize the amount of block cutting used in making fields. In response to the need for a simple flexible method of field shaping, a new adjustable blocking system was developed which allows a greater range of field adjustment with fewer blocks.

The system allows a wide latitude of placement of the shielding blocks on the blocking tray. The blocking system has been shown to be cost effective and allows rapid setup of treatment fields. It also allows daily blocking adjustment if required and has been shown to produce high quality reproducible fields in clinical use. This system also affords the advantage of allowing easy field adjustment on a daily basis, e.g. lens blocks on bilateral whole brain fields. This system is also cost effective since the mounted blocks can be used repeatedly thereby reducing the time and material required to fabricate customized cast blocks.

The primary improvement over the prior art with the instant invention is that it allows for a great degree of perimeter field adjustment not available in the prior art.

Another improvement is that the invention allows for easy adjustment of both perimeter and interior blocking.

Another improvement is that the invention allows for an inexpensive and reproduceable product and method for using the product for shaping electromagnetic fields.

These and other improvements will become obvious from the drawings and specifications and drawings attached hereto on which like numerals represent like portions of the invention.

BRIEF DESCRIPTION OF THE DRAWINGS

For a further understanding of the nature and objects of the present invention, reference should be made to the following detailed description taken in conjunction with the accompanying drawings in which like parts are given like reference numerals and wherein.

GENERAL DISCUSSION OF THE INVENTION

Detailed Discussion of the Preferred Embodiment(s)

Figure 1:
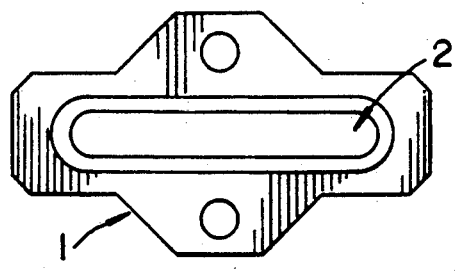
FIG. 1 is a plan view of a connection flange envisioned for use with the invention.
Figure 2:
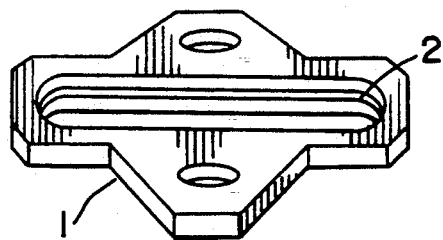
FIG. 2 is a perspective view of the flange shown in FIG. 1.
Figure 3:
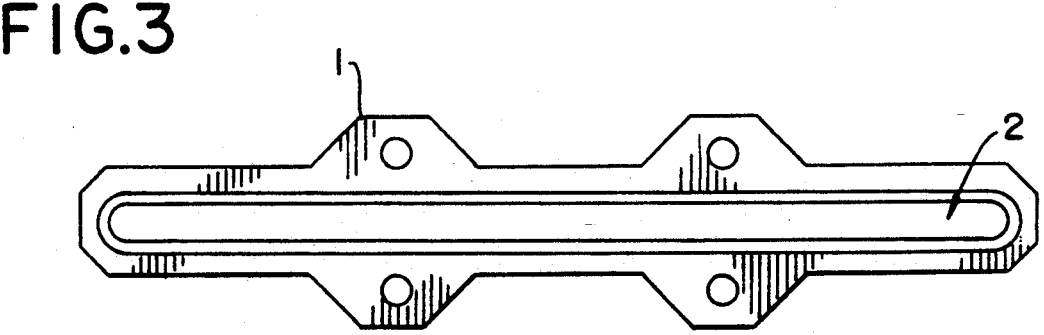
FIG. 3 is plan view of an alternately elongated flange which may be used in the invention.
Figure 4:
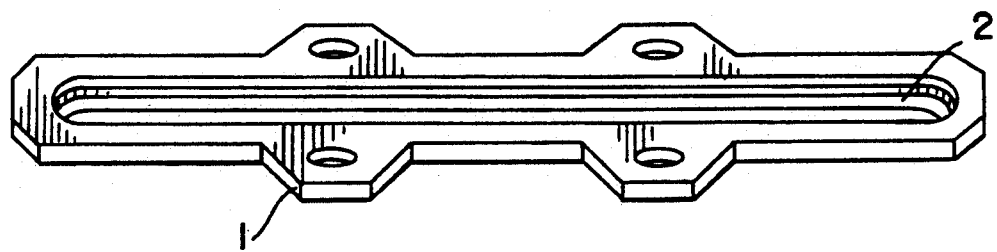
FIG. 4 is a perspective view of the flange shown in FIG. 3.
Figure 5:
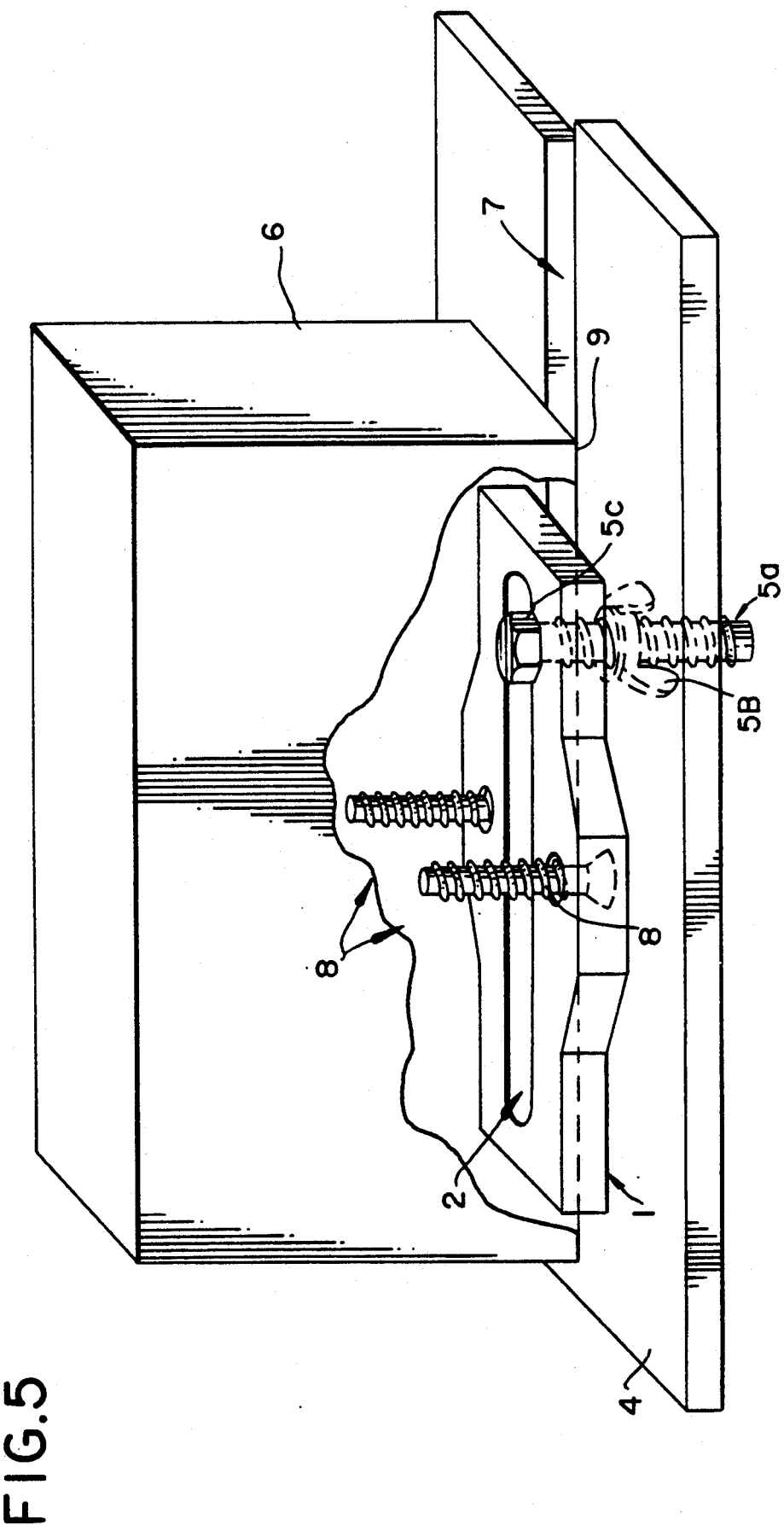
FIG. 5 is a perspective view of the invention encompassing the flange of FIG. 1 with the other elements.

To allow flexibility in shielding block placement, a set of connection flanges 1 were designed and built from stock aluminum. Two types of flanges 1 were designed. Small flanges for small shielding blocks 6 are shown in FIG. 5. Close up views of these flanges 1 are shown in FIGS. 1 and 2. The invention also envisioned large flanges 1 for larger blocks 6 which are shown in FIGS. 3 and 4. These large flanges 1 allow for a greater slot 2 length. The cost of fabrication of the flanges 1 is relatively modest. The key to the invention lies in the slot 2 which is defined by the flanges 1. Each flange allows both lateral and rotational movement of the attached block 6 free from the rotation and lateral movement of the connecting mounting means 6 to the tray 4 in FIG. 5.

Figure 6:
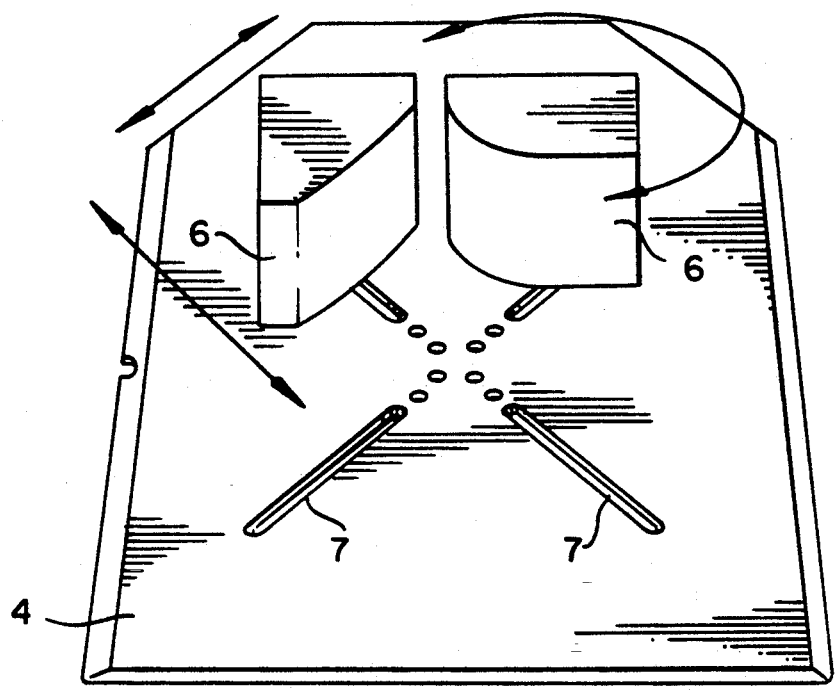
FIG. 6 shows a plan view of a tray designed to attain maximum use of the invention herein, showing rotational and longitudinal movement.

As can best be seen in FIG. 6, a special tray 4, can be used with tray slots 7.

In the preferred embodiment, these flanges 1 are attached to cast Lipowitz's metal blocks 6 of the desired shape by countersunk flat head metal screws 8. The flanges 1 are attached to the base 9 of the shielding blocks 6 in a position so that the flanges 1 do not protrude into the treatment field. In this regard it is important to construct each shielding block 6 in a size that will allow sufficient room at the base for adequate positioning and attachment of the chosen flange 1.

With this technique, a small number of curved, square and triangular shielding blocks 6 can handle a wide variety of clinical situations. Since the blocks are designed to be adjustable, this will result in variable field penumbra depending on their position on the blocking tray. Parallel sided shielding blocks may be used in many cases with acceptable results. The penumbra effect can be reduced if desired by constructing the blocks 6 positioned at the common sites of placement on the blocking tray 4 and incorporating beam deliverance into each shielding block 6.

The flanges 1 with their mounted blocks 6 are then connected to the Lucite or polycarbonate blocking tray 4 by the mounting means 5. In the preferred embodiment, the mounting means, 5 comprises a machine bolt 5(a) and wing nut or thumb screw 5(b) as shown in FIG. 5. The head 5(c) of the machine bolt 5(a) can move in a slotted track 2 in the flange 1 to allow lateral motion of the attached block 6. The mounted blocks 6 can also be rotated 360 degrees in either direction. To allow an additional dimension to the flexibility of block adjustment slotted tracks are machined into the blocking trays 4. The latitudes of motions of two blocks with flanges mounted on a tray are shown in FIG. 6.

PROCESS

The process by which the above described invention is used comprises the following table.

TABLE 1

| |
|---|
| 1. selecting the appropriate blocks to be used of the type described in the disclosure. |
| 2. Selecting the flanges corresponding to the blocks selected in step 1 |
| 3. Attaching the selected slotted tral to the simulator. |
| 4. Attaching the selected blocks onto corresponding flanges |
| 5. Movably attaching the flanges onto the tray at a location approximating the perimeter or internal shielding location. |
| 6. Fluoroscoping a target while simultaneously adjusting the perimeter blocks on the tray so as to obtain the shape desired for the perimeter |
| 7. Fluoroscoping a target while simultaneously adjusting the internal blocks on the tray so as to obtain the shape desired for the internal blocking |
| 6(a)/7(a) adjustment using the invention described herein along the (i) horizontal, (ii) vertical and (iii) rotational axis as may be required. |
| 8. Fixing the perimeter and internal blocks in place with the mounting means of the flange |
| 9. Marking the Lucite tray with the position of the blocks |
| 10. Treating using standard radiation techniques. |

Field set up is accomplished by selecting the appropriate blocks to be used step 1, selecting the corresponding flanges step 2, attaching the slotted Lucite tray in the simulator tray slot step 3, and attaching the blocks to the corresponding flanges step 4.

The adjustment is made by movably mounting the flanges with the corresponding blocks to the tray step 5 and, while using fluoroscopy or any similar technique to observe the field generate, adjusting the perimeter blocks step 6 and the internal blocks step 7. The blocks can be positioned horizontally step 6(a)(i) and 7(a)(i), vertically step 6(a)(ii) and 7(a)(ii) and rotationally 6(a)(iii) and 7(a)(iii) to obtain the desired shape in the desired location.

Once the block is in satisfactory position fixing the perimeter and internal blocks in place with the mounting means of the flange is accomplished step 8, the mounting means, the wing bolt or thumb screw arrangement 5 described as above, is tightened to secure the block to the tray. The block position on the Lucite trays can also be marked to insure reproducibility of block placement step 9.

This system allows field fabrication during simulation so that treatment can commence immediately without the necessitated delay required for manufacturing of customized cast blocks. This can be of particular benefit in cases of palliative treatment.

Once the positions of the adjustable blocks are defined on the tray for a particular field, the mounted blocks can be used with a linear accelerator or cobalt unit for daily patient treatment step 18.

Figure 7A:
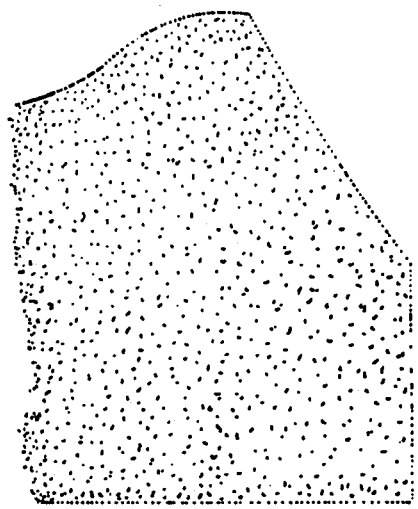
FIG. 7 shows a photograph of a perimeter defined by the invention.
Figure 7B:
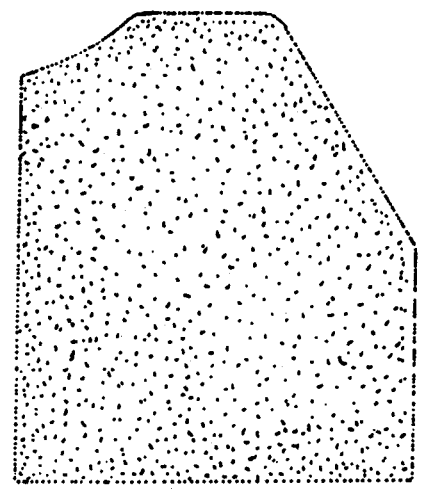
Figure 8:
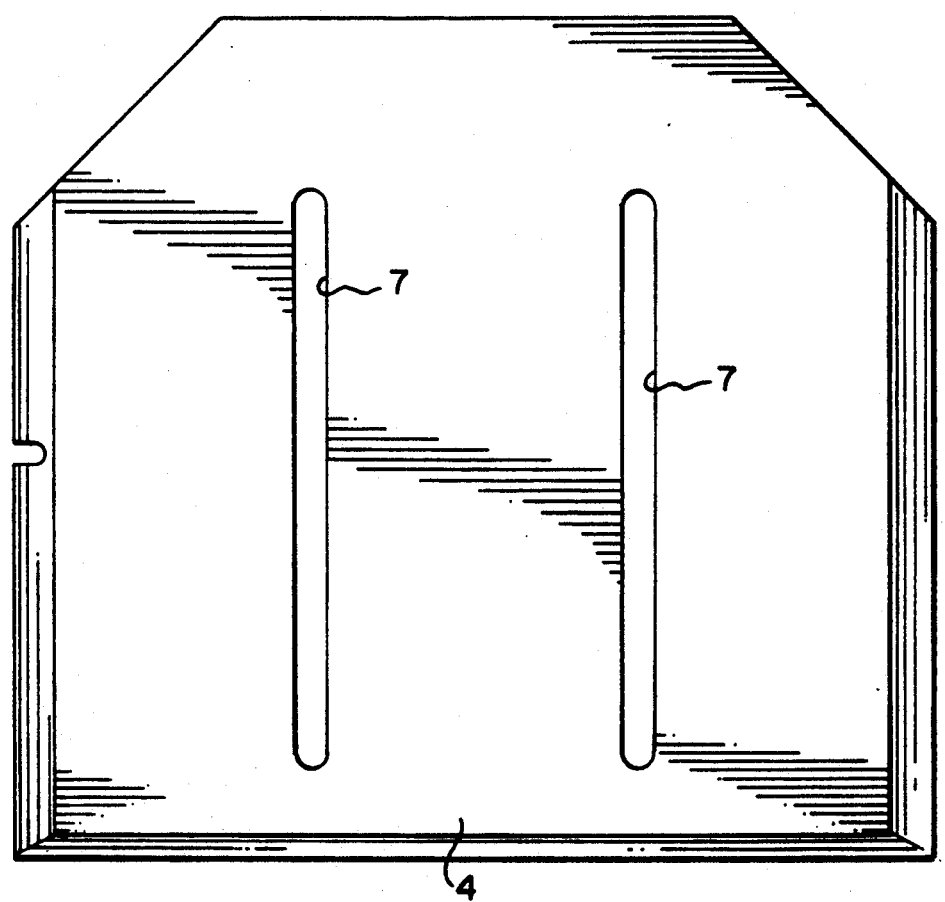
FIG. 8 shows a plan view of a tray designed to show a tray with two slots running perpendicular to each other.

In general, the fields created by this blocking system are quite acceptable. FIG. 7 shows a comparison of port films from a custom block of Lipowitz's metal and a field fashioned from a set of adjustable blocks respectively. This system also affords the advantage of allowing easy field adjustment on a daily basis, e.g. lens blocks on bilateral whole brain field.

What is claimed is:

1. A device for blocking radiation, typically electron beam and X-ray radiation, from specific areas comprising:
   a. at least one connection flange defining a slot providing for lateral and rotational movement;
   b. at least one shielding block which is larger than said connection flange;
   c. a blocking tray having at least one slotted track;
   d. a mounting means allowing rotational and lateral movement between the connection flange and the shielding block.

2. The device of claim 1 wherein the device further comprises at least two connecting flanges.

3. The device of claim 2 wherein one of the two connection flanges is smaller than the other.

4. The device of claim 2 wherein the shielding tray has at least two transversely mounted slots.

5. The device of claim 4 wherein the shielding tray has two slots running perpendicular to each other.

6. The device of claim 1 wherein the slot defined by the flange is as wide as structurally allowable while allowing the narrowest shielding block to be used with the device to extend beyond the boundaries of the connection flange.

7. The device of claim 1 wherein the mounting herein comprises a bolt passing through the slot into a wing nut.

8. A method of designing customized perimeter and internal electromagnetic fields using a blocking tray having at least one slotted track; at least one connection flange defining a slot providing for lateral and rotational movement; and at least one shielding block prior to treating the patient using standard radiation techniques comprising the following steps;
   a. selecting shielding blocks to be used as a perimeter block or an internal block;
   b. Selecting at least one flange corresponding to the blocks selected in step a;
   c. Attaching the selected slotted tray to the simulator;
   d. Attaching the selected perimeter or internal blocks onto the corresponding flange from step b;
   e. Movably attaching at least one flange from step b onto the tray at a location approximating the perimeter or internal shielding location;
   f. Fluoroscoping a target while simultaneously adjusting the perimeter blocks on the tray so as to obtain the shape desired for the perimeter along the (i) horizontal, (ii) vertical and (iii) rotational axis;
   g. Fluoroscoping a target while simultaneously adjusting the internal blocks on the tray so as to obtain the shape desired for the internal blocking along the (i) horizontal, (ii) vertical and (iii) rotational axis.

9. The invention of claim 8 comprising the additional step of:
   h. Fixing the perimeter and internal blocks in place.

10. The invention of claim 8 comprising the additional step of:
   h. Marking the slotted tray with the position of the blocks.

* * * * *